United States Patent
Spiessens et al.

(10) Patent No.: US 12,186,592 B2
(45) Date of Patent: Jan. 7, 2025

(54) RADIOTHERAPY DOSE ANALYSIS METHODS AND SYSTEMS

(71) Applicants: Varian Medical Systems Particle Therapy GmbH & Co. KG, Troisdorf (DE); VARIAN MEDICAL SYSTEMS, INC., Palo Alto, CA (US)

(72) Inventors: Sylvie Spiessens, Desselgem (BE); Michael Folkerts, Carrollton, TX (US); Eric Abel, San Jose, CA (US); Isabel Huth, Kuerten (DE); Tina Pfeiler, Cologne (DE); Pierre Lansonneur, Helsinki (FI)

(73) Assignee: VARIAN MEDICAL SYSTEMS PARTICLE THERAPY GMBH & CO. KG, Troisdorf (DE)

( * ) Notice: Subject to any disclaimer, the term of this patent is extended or adjusted under 35 U.S.C. 154(b) by 341 days.

(21) Appl. No.: 17/563,882

(22) Filed: Dec. 28, 2021

(65) Prior Publication Data

US 2023/0201630 A1 Jun. 29, 2023

(51) Int. Cl.
*A61N 5/10* (2006.01)

(52) U.S. Cl.
CPC ......... *A61N 5/1071* (2013.01); *A61N 5/1039* (2013.01); *A61N 5/1075* (2013.01)

(58) Field of Classification Search
None
See application file for complete search history.

(56) References Cited

U.S. PATENT DOCUMENTS

| | | | |
|---|---|---|---|
| 2006/0193435 A1* | 8/2006 | Hara | A61N 5/1049 378/65 |
| 2016/0136459 A1* | 5/2016 | Verhaegen | A61N 5/1071 378/165 |
| 2017/0248702 A1* | 8/2017 | Norrell | G01T 1/02 |
| 2018/0243586 A1 | 8/2018 | Ramezanzadeh Moghadam et al. | |
| 2019/0054320 A1* | 2/2019 | Owens | A61N 5/1071 |
| 2020/0282231 A1* | 9/2020 | Khuntia | A61N 5/1038 |
| 2020/0282234 A1 | 9/2020 | Folkerts et al. | |
| 2020/0286601 A1 | 9/2020 | Khuntia et al. | |
| 2020/0289853 A1* | 9/2020 | Friedman | A61N 5/1064 |
| 2020/0376299 A1* | 12/2020 | Hautvast | A61B 34/20 |
| 2020/0384289 A1* | 12/2020 | Smith | G16H 50/20 |
| 2021/0016108 A1* | 1/2021 | Khuntia | A61N 5/1043 |

(Continued)

OTHER PUBLICATIONS

B. Yang et al. 'Development of a novel methodology for QA of respiratory-gated and VMAT beam delivery using Octavius 4D phantom' *Medical Dosimetry*, 44, 2019, pp. 83-90.

*Primary Examiner* — Marcus H Taningco
(74) *Attorney, Agent, or Firm* — Harness, Dickey & Pierce, P.L.C.

(57) ABSTRACT

Dose analysis radiotherapy systems and methods for determine delivered radiotherapy dose, dose rate, irradiation time and position information and planned radiotherapy dose, dose rate, irradiation time and position information. The dose analysis systems and methods further compare the as delivered dose, dose rate, irradiation time and position information to the planned dose, dose rate, irradiation time and position information to generate a graphical representation of one or more of the delivered dose, dose rate, irradiation time and position information versus planned dose, dose rate, irradiation time and position information.

17 Claims, 4 Drawing Sheets

(56) References Cited

U.S. PATENT DOCUMENTS

2021/0128946 A1    5/2021  Smith et al.
2021/0196981 A1*   7/2021  Bondar ................ A61N 5/1038
2022/0001206 A1*   1/2022  Ropo .................... A61N 5/103

* cited by examiner (Conventional Art)
FIG. 1

RADIOTHERAPY DOSE ANALYSIS METHODS AND SYSTEMS

BACKGROUND OF THE INVENTION

Radiotherapy can be used in the treatment of cancer, tumors, lesion, and the like. Radiotherapy involves directing a beam of high energy radiation, such as but not limited to charged particles, (e.g., ions), protons, electrons, or photons (e.g., x-ray, Gamma), into a target volume. One of the goals of radiotherapy treatment is to maximize the dose supplied to a target, such as a tumor, while minimizing the dose absorbed by the surrounding tissue. A treatment plan is used to specify various aspects of the radiotherapy to deliver sufficient radiation to unhealthy tissue in the target volume, while minimizing exposure of surrounding healthy tissue.

Figure 1:
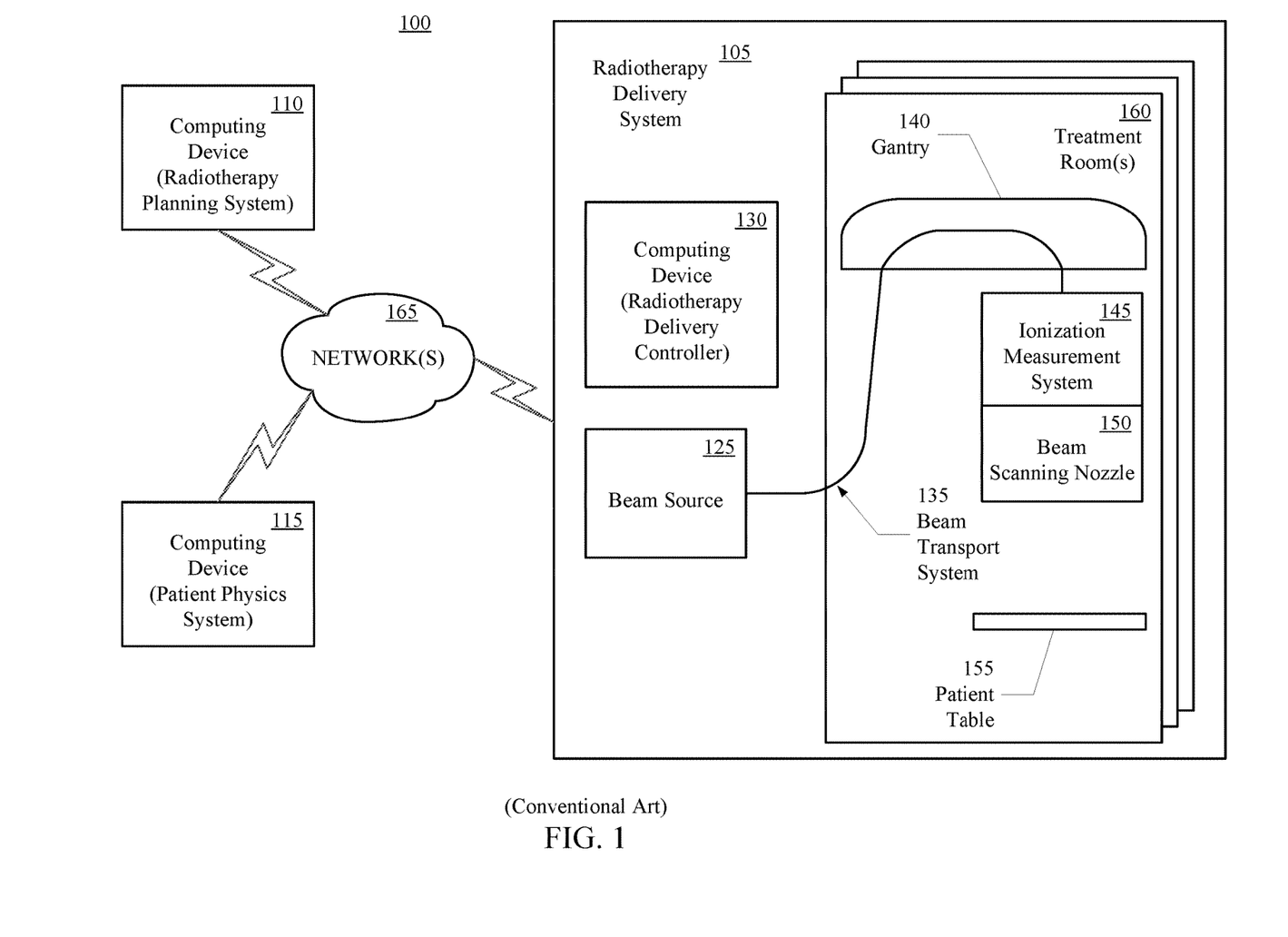
FIG. 1 shows an exemplary radiotherapy system according to the conventional art.

Referring to FIG. 1, an exemplary radiotherapy system according to the conventional art is shown. The radiotherapy system 100 can include a radiotherapy delivery system 105, and optionally a radiotherapy planning system 110, a patient physics system 115 and/or the like communicatively coupled to the radiotherapy delivery system 105. The radiotherapy delivery system 105 can include, but is not limited to, a beam source 125, one or more radiotherapy delivery controllers 130 and one or more beam transport systems 135. The radiotherapy delivery system 105 can further include a gantry 140, ionization measurement system 145, beam scanning nozzle 150 and a patient table 155 disposed in each of one or more treatment rooms 160. The beam source 125 can be coupled to the gantry 140, ionization measurement device 145 and beam scanning nozzle 150 of the respective treatment room 160 by the beam transport system 135. The beam transport system 135 can be configured to focus and shape energy beams and guide them to the gantries 140 in the one or more treatment rooms 160. The gantry 140 can rotate about the patient on the patient table 155 to deliver the energy beam at any angle while minimizing the need to reposition the patient. The patient table 155 can include a sophisticated patient positioning system that moves in one or more directions to position patients. The beam scanning nozzle 150 can be configured to scan a broad beam, a pencil beam or the like about a target area of the patient. The ionization measurement system 145 can include an array of detectors and a sampling processor configured to sample charge values between ionization chamber plates of the array of ionization detectors to determine dose, time and position parameters of or associated with charged particles (e.g., ions), protons, electrons, photons (e.g., x-ray, Gamma) or the like radiation stream.

The one or more radiotherapy delivery controllers 130 can be configured to control the operation of the beam source 125, the beam transport systems 135, the gantries 140, ionization measurement systems 145, beam scanning nozzles 150 and/or patient tables 155. One or more computing devices 110 can also be configured to generate patient radiotherapy treatment plans. One or more computing devices 115 can also be configured to generate patient physics such as, but not limited to, Computer Tomography (CT) scan images, Magnetic Resonance Imaging (MM) scan images, Positron-Emission Tomography (PET) images and/or ultrasound images or the like. The one or more computing devices 110, 115, 130 can include one or more processors, one or more memories, one or more network interfaces, and one or more input/output devices, such as keyboards, pointing devices, displays and/or the like, coupled together by one or more busses. The one or more computing devices 110, 115, 130 can be any type of computing device, including but not limited to desktop Personal Computers (PCs), laptop PCs, server computer, virtual machine, cloud computing platform, or the like. The one or more computing devices 110, 115, 130 can be coupled directly to each other, and/or can be coupled through one or more networks 165, including Local Area Networks (LAN), Wide Area Networks (WAN), the Internet or the like. Alternatively or in addition, one or more of the computing devices 110, 115, 130 can be combined together and/or integral to one or more other subsystems of the radiotherapy system 100.

In many cases, radiation can be delivered to the target tissue with sub-millimeter precision, while mostly sparing normal tissue, ultimately leading to killing cells in the target tissue. However, the tumor cells' ability to escape the cell killing effects of radiation and/or to develop resistance mechanisms can counteract the cell killing effect of radiotherapy, potentially limiting the therapeutic effect of radiotherapy. Furthermore, delivery of ultra-high dose radiation, in radiotherapy treatment techniques such as FLASH treatment plans, are believed to spare normal tissue from radiation-induced toxicity. The treatment outcome regarding the target and toxicity to the surrounding tissue not only depends on physical parameters, such as dose, but also depend on a multitude of biological parameters that may or may not be known prior to and/or during the time of treatment. Currently, treatment plans are based on physical dose, which can be displayed in three-dimensions. Most treatment plans only use dosimetric endpoint goals as a proxy for biological impact, such as, "do not exceed max spinal cord dose of x." Accordingly, there is a continuing need for improved analytic tools for physical and biological parameters in radiotherapy treatment.

SUMMARY OF THE INVENTION

The present technology may best be understood by referring to the following description and accompanying drawings that are used to illustrate embodiments of the present technology directed toward radiotherapy dose analysis methods and systems.

In one embodiment, a radiotherapy dose analysis system can include a delivery information extractor, a physics dose model engine and a dose/dose rate comparison engine. The delivery information extractor can be configured to determine delivered radiotherapy treatment information including dose, irradiation time and position information. The physics dose model engine can be configured to determine planned flash treatment information including dose, dose rate, irradiation time and position information from a radiotherapy treatment plan. The dose/dose rate comparison engine can be configured to reconstruct dose and dose rate information in two or three dimensions from dose, time and position information. The dose/dose rate comparison engine can be further configured to compare the dose, dose rate, irradiation time and position information of the delivered flash treatment information to the dose, dose rate, irradiation time and position information of the planned flash treatment plan and generate a graphical representation of one or more of the delivered dose, dose rate, irradiation time and position information versus planned dose, dose rate, time and position information.

In another embodiment, a radiotherapy dose analysis method can include determining as delivered radiotherapy treatment information including dose, dose rate, time and position information. Planned radiotherapy treatment information including dose, dose rate, time and position information can be determined from a radiotherapy treatment plan and patient physics records. The dose, dose rate, time and position information of the delivered radiotherapy treatment information can be compared to the dose, dose rate, time and position information of the planned radiotherapy treatment plan to generate a graphical representation of the delivered dose, dose rate, time and position information versus planned dose, dose rate, time and position information. The graphical representation of one or more of the delivered dose, dose rate, time and position information versus planned dose, dose rate, time and position information can be output on a display, saved in memory for further analysis, or the like.

In yet another embodiment, computing device executable instructions stored on one or more computing device readable media can be executed by one or more processors to perform a radiotherapy dose analysis method including determining as delivered radiotherapy treatment information including dose, dose rate, irradiation time and position information. Planned radiotherapy treatment information including dose, dose rate, irradiation time and position information can be determined from a radiotherapy treatment plan and patient physics records. The dose, dose rate, irradiation time and position information of the delivered radiotherapy treatment information to the dose, dose rate, irradiation time and position information of the planned radiotherapy treatment plan can be compared to generate a graphical representation of the delivered dose, dose rate, irradiation time and position information versus planned dose, dose rate, irradiation time and position information.

This Summary is provided to introduce a selection of concepts in a simplified form that are further described below in the Detailed Description. This Summary is not intended to identify key features or essential features of the claimed subject matter, nor is it intended to be used to limit the scope of the claimed subject matter.

BRIEF DESCRIPTION OF THE DRAWINGS

Embodiments of the present technology are illustrated by way of example and not by way of limitation, in the figures of the accompanying drawings and in which like reference numerals refer to similar elements and in which.

DETAILED DESCRIPTION OF THE INVENTION

Reference will now be made in detail to the embodiments of the present technology, examples of which are illustrated in the accompanying drawings. While the present technology will be described in conjunction with these embodiments, it will be understood that they are not intended to limit the technology to these embodiments. On the contrary, the invention is intended to cover alternatives, modifications and equivalents, which may be included within the scope of the invention as defined by the appended claims. Furthermore, in the following detailed description of the present technology, numerous specific details are set forth in order to provide a thorough understanding of the present technology. However, it is understood that the present technology may be practiced without these specific details. In other instances, well-known methods, procedures, components, and circuits have not been described in detail as not to unnecessarily obscure aspects of the present technology.

Some embodiments of the present technology which follow are presented in terms of routines, modules, logic blocks, and other symbolic representations of operations on data within one or more electronic devices. The descriptions and representations are the means used by those skilled in the art to most effectively convey the substance of their work to others skilled in the art. A routine, module, logic block and/or the like, is herein, and generally, conceived to be a self-consistent sequence of processes or instructions leading to a desired result. The processes are those including physical manipulations of physical quantities. Usually, though not necessarily, these physical manipulations take the form of electric or magnetic signals capable of being stored, transferred, compared and otherwise manipulated in an electronic device. For reasons of convenience, and with reference to common usage, these signals are referred to as data, bits, values, elements, symbols, characters, terms, numbers, strings, and/or the like with reference to embodiments of the present technology.

It should be borne in mind, however, that these terms are to be interpreted as referencing physical manipulations and quantities and are merely convenient labels and are to be interpreted further in view of terms commonly used in the art. Unless specifically stated otherwise as apparent from the following discussion, it is understood that through discussions of the present technology, discussions utilizing the terms such as "receiving," and/or the like, refer to the actions and processes of an electronic device such as an electronic computing device that manipulates and transforms data. The data is represented as physical (e.g., electronic) quantities within the electronic device's logic circuits, registers, memories and/or the like, and is transformed into other data similarly represented as physical quantities within the electronic device.

In this application, the use of the disjunctive is intended to include the conjunctive. The use of definite or indefinite articles is not intended to indicate cardinality. In particular, a reference to "the" object or "a" object is intended to denote also one of a possible plurality of such objects. The use of the terms "comprises," "comprising," "includes," "including" and the like specify the presence of stated elements, but do not preclude the presence or addition of one or more other elements and/or groups thereof. It is also to be understood that although the terms first, second, etc. may be used herein to describe various elements, such elements should not be limited by these terms. These terms are used herein to distinguish one element from another. For example, a first element could be termed a second element, and similarly a second element could be termed a first element, without departing from the scope of embodiments. It is also to be understood that when an element is referred to as being "coupled" to another element, it may be directly or indirectly connected to the other element, or an intervening element may be present. In contrast, when an element is referred to as being "directly connected" to another element, there are not intervening elements present. It is also to be understood that the term "and/or" includes any and all combinations of one or more of the associated elements. It is also to be understood that the phraseology and terminology used herein is for the purpose of description and should not be regarded as limiting.

Figure 2:
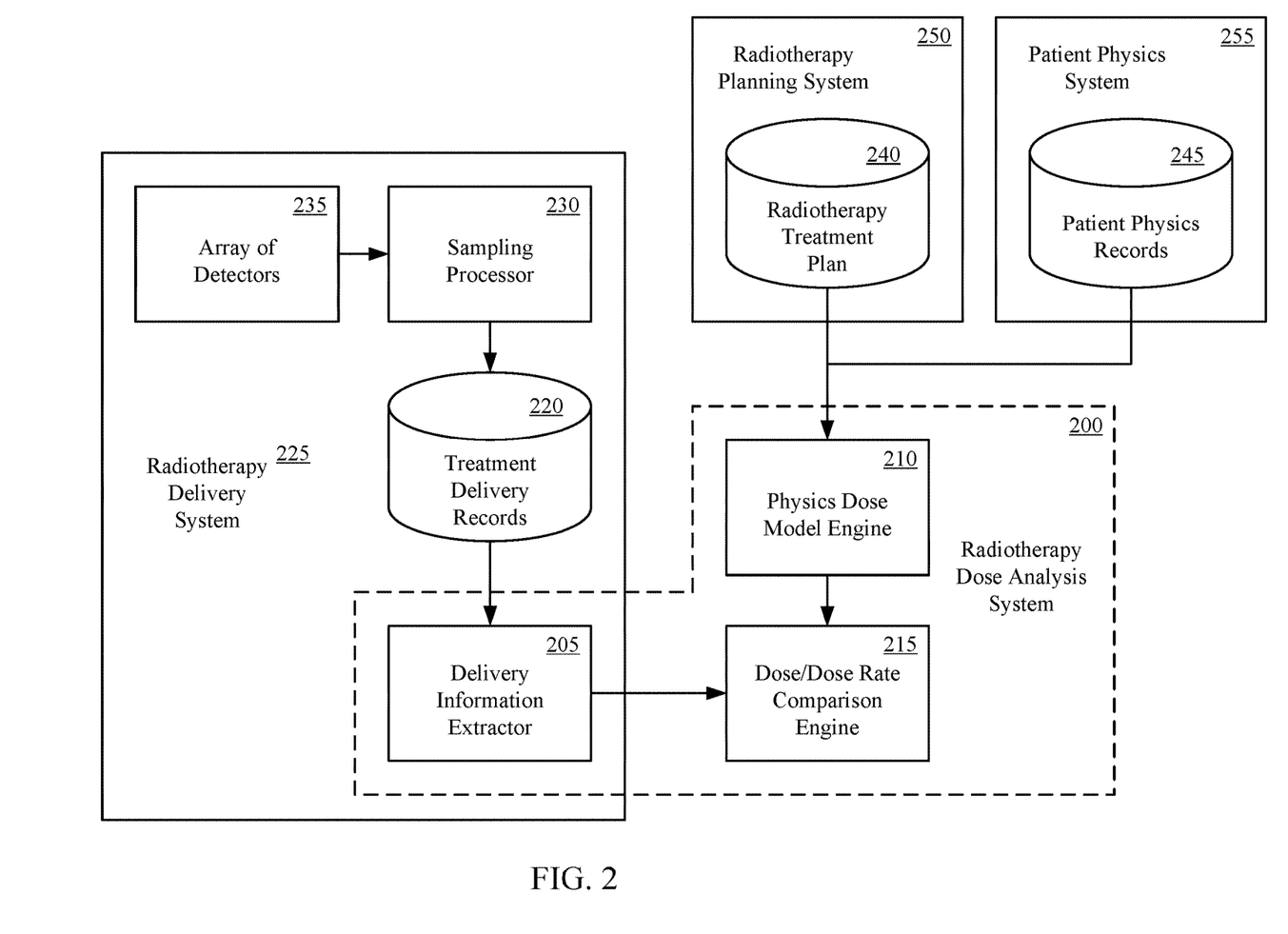
FIG. 2 shows a radiotherapy dose analysis system, in accordance with aspects of the present technology.

Referring now to FIG. 2, a radiotherapy dose analysis system, in accordance with aspects of the present technology, is shown. The radiotherapy dose analysis system 200 can include a delivery information extractor 205, a physics dose model engine 210 and a dose/dose rate comparison engine 215. The delivery information extractor 205 can be configured to determine delivered radiotherapy treatment information including dose, time and position information from treatment delivery records 220 of a radiotherapy delivery system 225. The radiotherapy delivery system 225 can be an intensity modulated radiation therapy (IMRT) or intensity modulated particle therapy (IMPT) system, wherein the beam intensity is varied across the target volume. Depending upon the treatment modality, the degrees of freedom available for intensity modulation can include, but not limited to, beam shaping (collimation), beam weighting (spot scanning) and angle of incidence (beam geometry). In one implementation, the radiotherapy system 225 can be a high dose rate radiotherapy system, such as a FLASH radiotherapy system or the like. High dose rate radiotherapy delivers high doses of radiation at high speeds, or short irradiation times, of 40 Gy/s and above. Exemplary FLASH therapy treatment plans can comprise delivering 40, 50, 100 Gy or more in one second or less. Studies have shown that delivering radiotherapy at such high dose rates allow comparable tumor control while sparing the healthy tissue thereby reducing toxicities.

In one implementation, the treatment delivery records 220 can include a data structure including dose, time and position information for one or more treatment sessions, patients and/or the like. For example, the treatment delivery records 220 can include logfiles including but not limited to dose, dose rate, and irradiation time for treatment sessions for each of one or more patients. In one implementation, a target, and optionally the surrounding tissue, can be represented by a volume. Optionally, one or more sub-volumes can also be represented in the target volume, and the surrounding tissue. One or more attributes and attribute values can be associated with the volume, and one or more attributes and attribute values can also be associate with the sub-volumes. The sub-volumes can represent anatomical structures, such as bones, organs and the like. The sub-volumes can also represent dose, dose rate and the like treatment attributes and/or attribute values. A voxel can represent each of an array of elements of volume of a three-dimensional space, especially each of an array of discrete elements into which a representation of a three-dimensional object is divided. A voxel can also represent a sample set of data, data point set, volume or the like on a regularly spaced, three-dimensional grid. Accordingly, one or more attributes and attribute values can also be associated with corresponding voxels. In one implementation, treatment parameters and biological parameters can be recorded, analyzed and/or displayed on a voxel-by-voxel basis. The treatment parameters can include dose, dose rate, irradiation time, beam size, beam overlap, beam energy, and/or the like, associated with corresponding voxels of a treatment map. The biological parameters can include toxicity levels, systemic biomarkers, genetic biomarkers, and/or the like.

In one implementation, the treatment delivery records 220 can be generated by a sampling processor 230 coupled to an array of detectors 235. For example, the sampling processor 230 can sample charge values between ionization chamber plates of an array of ionization detectors to determine dose, time and position parameters of or associated with a charged particle (e.g., ion), proton, electron, photon (e.g., x-ray, Gamma) or the like radiation stream. In one implementation, the delivery information extractor 205 can retrieve dose, time, position and the like parameters stored in the treatment delivery records 220 for input to the dose/dose rate comparison engine 215. In one implementation, the dose/dose rate comparison engine 215 can extract dose information (e.g., spot monitor unit (MU)) delivered for a given time (e.g., spot timing), and location (e.g., spot position) in a two- or three-dimensional plane, at each of one or more given depths of interest (e.g., one or more planes). In one implementation, the dose/dose rate comparison engine 215 can receive calibration information, such as but not limited to, depth of interest, spot size and dose per monitor unit (MU). The dose/dose rate comparison engine 215 can utilize the dose, time and position parameters along with the calibration information to reconstruct dose rate distribution information at the depth of interest. In one implementation, the delivery information extractor 205 can further utilize statistical parameters, such as but not limited to, delivered dose threshold and dose rate threshold, at inputs to extract the fraction of voxels, in two or three dimensions, that are above a given dose threshold and/or given dose rate threshold.

The dose/dose rate comparison engine 215 can compute the dose rate at each of a plurality of voxels as the quotient of the given voxel's dose and an effective irradiation time. Each voxel's effective irradiation time can start when a cumulative dose rises above a predetermined threshold value and can stop when the cumulative dose reaches a planned dose minus the predetermined threshold value. Radiotherapy using pencil beam scanning or spot scanning can introduce additional considerations for defining dose rate since the dose at each point in a field is the sum of contributions from multiple asynchronous spots. While each beam spot has an instantaneous and average dose rates, the dose rate of any voxel within a pencil beam scanning field can be difficult to characterize. In an exemplary implementation, the total dose, D, delivered to location $\vec{x}$ within a full field application time $t_f$ can be expressed as:

$$D(\vec{x}) = d(\vec{x}, t_f)$$

with the corresponding average or field dose rate computed as $$\dot{D}_{field}(\vec{x}) = \frac{D(\vec{x})}{t_f}.$$

However, most of the dose accumulation at $\vec{x}$ may occur during a fraction of $t_f$. Considering for this purpose an effective irradiation time $$T(\vec{x}) = t_1 - t_0.$$

where $t_0$ and $t_1$ are defined in terms of $d(\vec{x}, t)$ by the expressions $$d(\vec{x}, t_0) = d^\dagger, \text{ and}$$

$$d(\vec{x}, t_1) = D(\vec{x}) - d^\dagger.$$

In other words, the effective irradiation time starts at $t_0$ when the accumulation dose at $\vec{x}$ exceeds a threshold dose of $d^\dagger$, and ends at $t_1$ when the accumulation dose comes within $d^\dagger$ of the total dose, $D\vec{x}$. In one implementation, the pencil beam spot dose rate at point $\vec{x}$ can be the quotient $$\dot{D}_{PBS}(\vec{x}) = \frac{D(\vec{x}) - 2d^\dagger}{T(\vec{x})}.$$

The physics dose model engine 210 can be configured to determined planned radiotherapy treatment information including dose, time and position information from a radiotherapy treatment plan 240 and patient physics records 245. In one implementation the physics dose model engine 210 can determine dose, time and position information based on a FLASH radiotherapy treatment plan or the like. The FLASH radiotherapy is a non-invasive therapy for the treatment of cancer, tumors and the like. FLASH radiotherapy delivers the treatment dose at ultra-high speeds, which are typically less than a second. Exemplary FLASH radiotherapy plans can specify delivery of ion particles at a dose rate of 40 grays per second (Gy/s) to 150 Gy/s. In one implementation, the radiotherapy treatment plan can be generated by a radiotherapy planning system 250. In one implementation, the patient physics records 245, such as but not limited to Computer Tomography (CT) scan images, Magnetic Resonance Imaging (MRI) scan images, Positron-Emission Tomography (PET) images and/or ultrasound images, can be generated by a patient physics system 255. The patient physics records can include geometric relations between images (commonly referred to as registrations), delineations of organs, tumors (commonly referred to as structures), and the like. For example, a computer tomography (CT) system can generate CT images of a target and surrounding tissue of a patient that can be utilized to determine structure, location, orientation, density and the like parameters of the target and surrounding tissue.

The dose/dose rate comparison engine 215 can be further configured to compare the dose, dose rate, irradiation time and position information of the delivered radiotherapy treatment information to the dose, dose rate, irradiation time and position information of the planned radiotherapy treatment plan and generate a graphical representation of one or more of the delivered dose, dose rate, irradiation time and position information versus planned dose, dose rate, irradiation time and position information. The dose/dose rate comparison engine 215 can also be configured to store the comparison results of the delivered dose, dose rate, irradiation time and position information versus planned dose, dose rate, irradiation time and position information. The as delivered treatment parameters and the parameters of the treatments plan will typically vary from each other. For example, the parameters, such as density, depth and the like of the physical structure of target tissue and surrounding tissue varies from patient to patient. Furthermore, the parameters of the physical structure of a given patient varies during treatments and/or between treatments as a result of patient position, respiration and the like. Similarly, the delivered radiation varies from machine to machine as a result of manufacturing and/or operating conditions. Therefore, there are variations in dose, dose rate, time, position and the like between the treatment plan and that delivered by the radiotherapy delivery system. The comparison of the delivered dose, dose rate, irradiation time and position information versus planned dose, dose rate, irradiation time and position information from the dose/dose rate comparison engine 215 can be utilized by a machine quality assurance (QA) tool and/or a patient QA tool.

The delivery information extractor 205, physics dose model engine 210 and dose/dose rate comparison engine 215 can be integral to one or more of the radiotherapy delivery system 225, radiotherapy planning system 250, and/or patient physics system 255. One or more of the delivery information extractor 205, physics dose model engine 210 and dose/dose rate comparison engine 215 can also be implemented by a separate computing device. The delivery information extractor 205, physics dose model engine 210 and dose/dose rate comparison engine 215 can be implemented as computing device-executable instructions (e.g., computer program) that are stored in computing device-readable media (e.g., computer memory) and executed by a computing device (e.g., processor).

Figure 3:
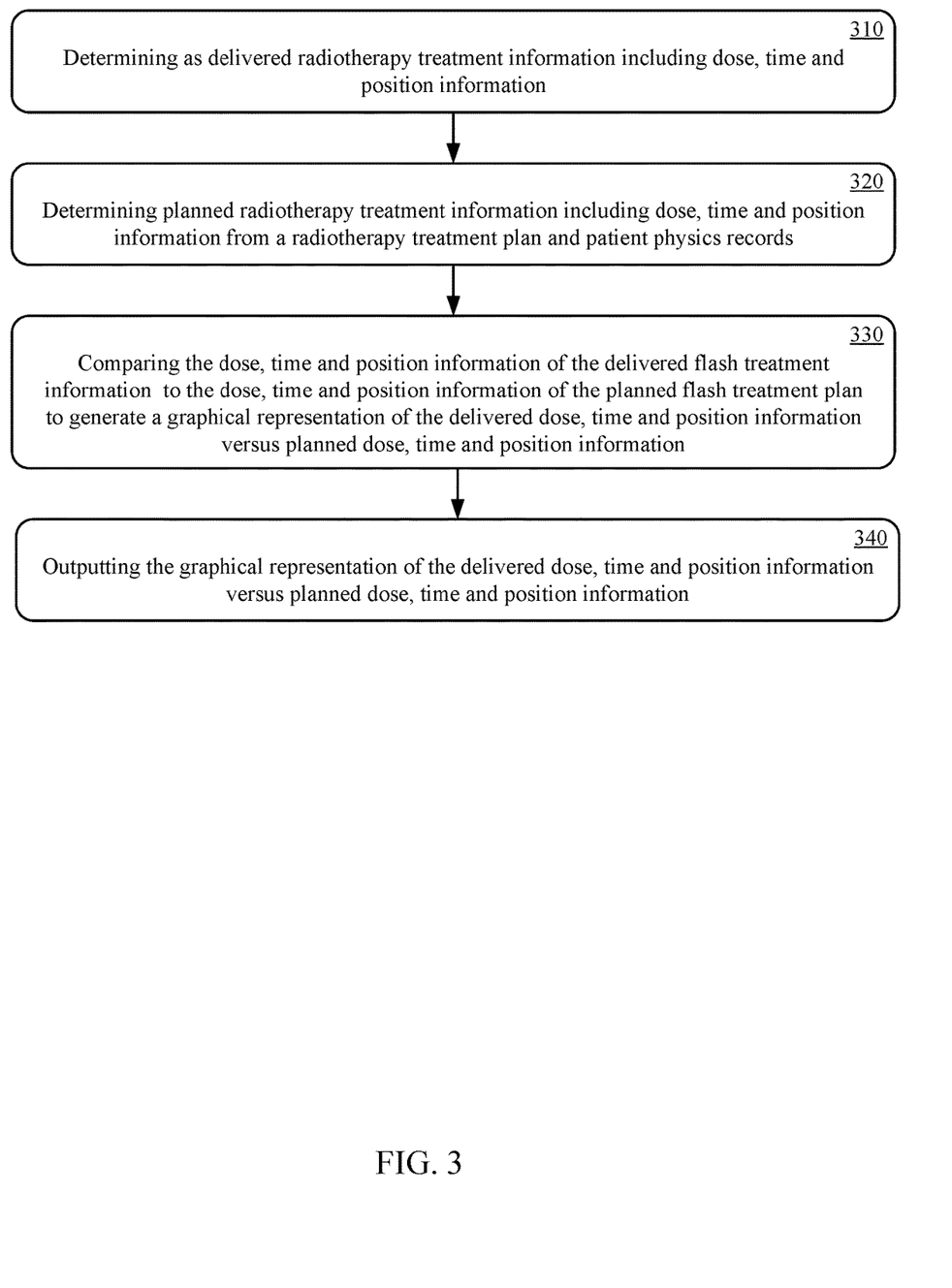
FIG. 3 shows a radiotherapy dose analysis method, in accordance with aspects of the present technology.

Referring now to FIG. 3, a radiotherapy dose analysis method, in accordance with aspects of the present technology, is shown. The method may be implemented as computing device-executable instructions (e.g., computer program) that are stored in computing device-readable media (e.g., computer memory) and executed by a computing device (e.g., processor). The method can include determining as delivered radiotherapy treatment information including dose, dose rate, irradiation time and position information, at 310. In one implementation, the delivered dose rate is determined from the delivered dose, irradiation time and position information.

The delivered radiotherapy treatment information can be determined from treatment delivery records of a radiotherapy delivery system. The radiotherapy delivery system can be an intensity modulated radiation therapy (IMRT) or intensity modulated particle therapy (IMPT) system, wherein the beam intensity is varied across the target volume. Depending upon the treatment modality, the degrees of freedom available for intensity modulation can include, but not limited to, beam shaping (collimation), beam weighting (spot scanning) and angle of incidence (beam geometry). In one implementation, the radiotherapy system can be a high dose rate radiotherapy system, such as a FLASH radiotherapy system or the like. High dose rate radiotherapy, or FLASH therapy, delivers high doses of radiation at high speeds, or short irradiation times, of 40 Gy/s and above. Exemplary FLASH therapy treatment plans can comprise delivering 40, 50, 100 Gy or more in one second or less. Studies have shown that delivering radio therapy at such high dose rates allow comparable tumor control while sparing the healthy tissue thereby reducing toxicities.

Again, the treatment delivery records can include a data structure including dose, dose rate, irradiation time and position information for one or more treatment sessions, patients and/or the like. For example, the treatment delivery records can include logfiles including but not limited to dose, dose rate, irradiation time for treatments sessions for each of one or more patients. In one implementation, a target, and optionally the surrounding tissue, can be represented by a volume. Optionally, one or more sub-volumes can also be represented in the target volume, and the surrounding tissue. One or more attributes and attribute values can be associated with the volume, and one or more attributes and attribute values can also be associate with the sub-volumes. The sub-volumes can represent anatomical structures, such as bones, organs and the like. The sub-volumes can also represent dose, dose rate and the like treatment attributes and/or attribute values. A voxel can represent each of an array of elements of volume of a three-dimensional space, especially each of an array of discrete elements into which a representation of a three-dimensional object is divided. A voxel can also represent a sample set of data, data point set, volume or the like on a regularly spaced, three-dimensional grid. Accordingly, one or more attributes and attribute values can also be associated with corresponding voxels. In one implementation, treatment parameters and biological parameters can be recorded, analyzed and/or displayed on a voxel-by-voxel basis. The treatment parameters can include dose, dose rate, irradiation time, beam size, beam overlap, beam energy, and/or the like, associated with corresponding voxels of a treatment map.

The biological parameters can include toxicity levels, systemic biomarkers, genetic biomarkers, and/or the like.

In one implementation, the treatment delivery records can be generated by a sampling processor coupled to an array of detectors. For example, the sampling processor can sample charge values between ionization chamber plates of an array of ionization detectors to determine dose, irradiation time and position parameters of or associated with a charged particle (e.g., ion), proton, electron, photon (e.g., x-ray, Gamma) or the like radiation stream. In one implementation, a delivery information extractor can retrieve dose, time, position and the like parameters from treatment delivery records for use by a dose/dose rate comparison engine. In one implementation, a dose/dose rate comparison engine can extract dose information (e.g., spot monitor unit (MU)) delivered for a given irradiation time (e.g., spot timing), and location (e.g., spot position) in a two- or three-dimensional plane, at each of one or more given depths of interest (e.g., one or more planes). In one implementation, the delivery information extractor can receive calibration information, such as but not limited to, depth of interest, spot size and dose per monitor unit (MU). The dose/dose rate comparison engine can utilize the dose, irradiation time and position parameters along with the calibration information to reconstruct dose rate distribution information at the depth of interest. In one implementation, the dose/dose rate comparison engine can further utilize statistical parameters, such as but not limited to, delivered dose threshold and dose rate threshold at inputs, to extract the fraction of voxels, in two or three dimensions, that are above a given dose threshold and/or given dose rate threshold.

In an exemplary implementation, the dose/dose rate comparison engine can compute the dose rate at each of a plurality of voxels as the quotient of the given voxel's dose and an effective irradiation time. Each voxel's effective irradiation time can start when a cumulative dose rises above a predetermined threshold value and can stop when the cumulative dose reaches a planned dose minus the predetermined threshold value. Radiotherapy using pencil beam scanning or spot scanning can introduce additional considerations for defining dose rate since the dose at each point in a field is the sum of contributions from multiple asynchronous spots. While each beam spot has an instantaneous and average dose rates, the dose rate of any voxel within a pencil beam scanning field can be difficult to characterize. In an exemplary implementation, the total dose, D, delivered to location $\vec{x}$ within a full field application irradiation time $t_f$ can be expressed as:

$$D(\vec{x}) = d(\vec{x}, t_f)$$

with the corresponding average or field dose rate computed as $$\dot{D}_{field}(\vec{x}) = \frac{D(\vec{x})}{t_f}.$$

However, most of the dose accumulation at $\vec{x}$ may occur during a fraction of $t_f$. Considering for this purpose an effective irradiation time $$T(\vec{x}) = t_1 - t_0.$$

where $t_0$ and $t_1$ are defined in terms of $d(\vec{x}, t)$ by the expressions $$d(\vec{x}, t_0) = d^\dagger, \text{ and}$$

$$d(\vec{x}, t_1) = D(\vec{x}) - d^\dagger$$

In other words, the effective irradiation time starts at $t_0$ when the accumulation dose at $\vec{x}$ exceeds a threshold dose of $d^\dagger$, and ends at $t_1$ when the accumulation dose comes within $d^\dagger$ of the total dose, $D(\vec{x})$. In one implementation, the pencil beam spot dose rate at point $\vec{x}$ can be the quotient $$\dot{D}_{PBS}(\vec{x}) = \frac{D(\vec{x}) - 2d^\dagger}{T(\vec{x})}.$$

At 320, planned radiotherapy treatment information including dose, dose rate, irradiation time and position information from a radiotherapy treatment plan and patient physics records can be determined. In one implementation, a physics dose model engine can determine dose, dose rate, irradiation time and position information based on a FLASH radiotherapy treatment plan or the like. The FLASH radiotherapy is a non-invasive therapy for the treatment of cancer, tumors and the like. FLASH radiotherapy delivers the treatment dose at ultra-high speeds, which are typically less than a second. Exemplary FLASH radiotherapy plans can specify delivery of ion particles at a dose rate of 40 grays per second (Gy/s) to 150 Gy/s. In one implementation, the radiotherapy treatment plan can be generated by a radiotherapy planning system. In one implementation, the patient physics records, such as but not limited to Computer Tomography (CT) scan images, Magnetic Resonance Imaging (MRI) scan images, Positron-Emission Tomography (PET) images and/or ultrasound images, can be generated by a patient physics system. The patient physics records can include geometric relations between images (commonly referred to as registrations), delineations of organs, tumors (commonly referred to as structures), and the like. For example, a computer tomography (CT) system can generate CT images of a target and surrounding tissue of a patient that can be utilized to determine structure, location, orientation, density and the like parameters of the target and surrounding tissue.

At 330, the dose, dose rate, irradiation time and position information of the delivered radiotherapy treatment information can be compared to the dose, dose rate, irradiation time and position information of the planned radiotherapy treatment plan to generate a graphical representation of one or more of the delivered dose, dose rate, irradiation time and position information versus planned dose, dose rate, irradiation time and position information. The comparison results of the delivered dose, dose rate, irradiation time and/or position information versus planned dose, dose rate, irradiation time and/or position information can be output on one or more display devices, printed, and/or stored on one or more computing device readable media, at 340. The as delivered treatment parameters and the parameters of the treatments plan will typically vary from each other. For example, the parameters, such as density, depth and the like of the physical structure of target tissue and surrounding tissue varies from patient to patient. Furthermore, the parameters of the physical structure of a given patient varies during treatments and/or between treatments as a result of patient position, respiration and the like. Similarly, the delivered radiation varies from machine to machine as a result of manufacturing and/or operating conditions. Therefore, there are variations in dose, dose rate, irradiation time, position and the like between the treatment plan and that delivered by the radiotherapy delivery system. The comparison of the delivered dose, dose rate, irradiation time and/or position information versus planned dose, dose rate, irradiation time and position information can be utilized by a machine quality assurance (QA) tool and/or a patient QA tool.

Figure 4:
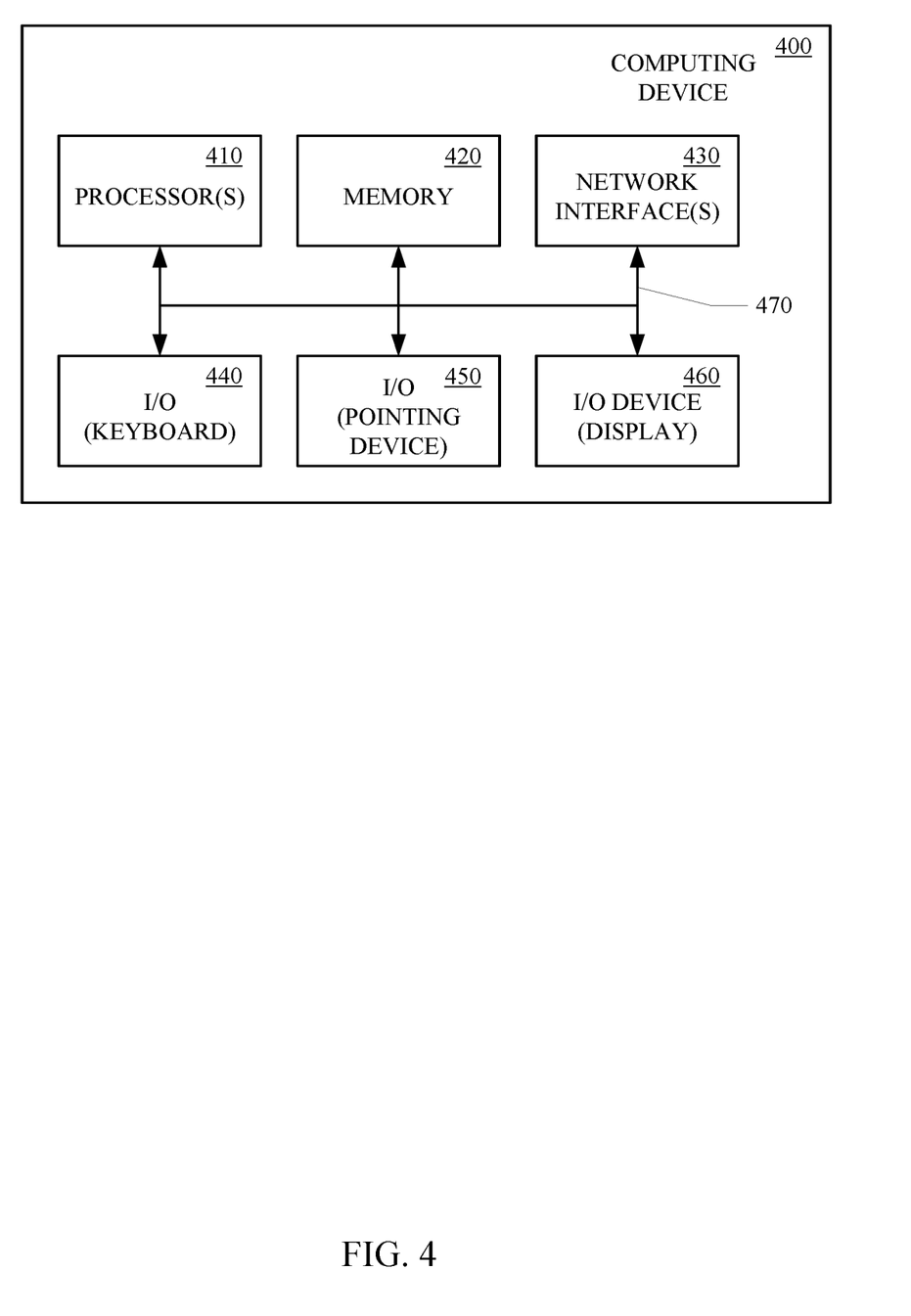
FIG. 4 shows an exemplary computing device for implementing aspects of the present technology.

Referring now to FIG. 4, a computing device for implementing one or more aspects of the present technology, is shown. The computing device 400 can include one or more processors 410, one or more memories 420, one or more network interface 430, and one or more input/output devices 440-460 such as keyboards, pointing devices, displays and/or the like, coupled together by one or more busses 470. The computing device 400 can be any type of computing device, including but not limited to desktop Personal Computers (PCs), laptop PCs, server computer, virtual machine, cloud computing platform, or the like. One or more software routines (e.g., computing device executable instructions) stored in the one or more memories (e.g., computing device readable media) 420, when executed by the one or more processors 410, can implement the radiotherapy dose analysis systems and methods as described above.

The foregoing descriptions of specific embodiments of the present technology have been presented for purposes of illustration and description. They are not intended to be exhaustive or to limit the present technology to the precise forms disclosed, and obviously many modifications and variations are possible in light of the above teaching. The embodiments were chosen and described in order to best explain the principles of the present technology and its practical application, to thereby enable others skilled in the art to best utilize the present technology and various embodiments with various modifications as are suited to the particular use contemplated. It is intended that the scope of the invention be defined by the claims appended hereto and their equivalents.

What is claimed is:

1. A radiotherapy dose analysis system comprising:
a delivery information extractor configured to determine delivered radiotherapy treatment information including dose, time and position information;
a physics dose model engine configured to determine planned radiotherapy treatment information including dose, dose rate, time and position information from a radiotherapy treatment plan; and
a dose/dose rate comparison engine configured to
receive calibration information and reconstruct a dose rate of the delivered radiotherapy treatment information from the calibration information and the dose, time and position information of the delivered radiotherapy treatment information,
reconstruct dose and dose rate information in two or three dimensions to compare the dose rate and the dose, time and position information of the delivered radiotherapy treatment information to the dose, dose rate, time and position information of the planned radiotherapy treatment plan and
generate a graphical representation of one or more of the dose rate and dose, dose rate, time and position information of the delivered radiotherapy treatment information versus the dose, dose rate, time and position information of the planned radiotherapy treatment plan.

2. The radiotherapy dose analysis system of claim 1, wherein the delivered radiotherapy treatment information including dose, time and position information is determined from one or more treatment delivery records.

3. The radiotherapy dose analysis system of claim 1, wherein the delivery information extractor is further configured to utilize statistical parameters including one or more of a delivered dose threshold and a dose rate threshold to extract fractions of voxels in two or three dimensions that are above one or more of the dose delivered threshold and dose rate threshold.

4. The radiotherapy dose analysis system of claim 2, further comprising:
an array of ionization detectors; and
a processor configured to sample charge values between ionization chamber plates of the array of ionization detectors to determine dose, time and position parameters for storage in the one or more treatment delivery records.

5. The radiotherapy dose analysis system of claim 1, wherein the physics dose model engine is further configured to determine the planned radiotherapy treatment information including the dose, dose rate, time and position information from patient physics information.

6. The radiotherapy dose analysis system of claim 5, wherein:
the radiotherapy treatment plan is generated by a radiotherapy planning system; and
the patient physics information is generated by a patient physics system providing one or more of a Computer Tomography (CT) scan image, a Magnetic Resonance Imaging (MRI) scan image, a Positron-Emission Tomography (PET) image and an ultrasound image.

7. The radiotherapy dose analysis system of claim 1, wherein radiotherapy treatment of the delivered radiotherapy treatment information and the planned radiotherapy treatment information comprises a flash radiotherapy treatment.

8. A radiotherapy dose analysis method comprising:
determining delivered radiotherapy treatment information including dose, irradiation time and position information;
determining planned radiotherapy treatment information including dose, dose rate, irradiation time and position information from a radiotherapy treatment plan and patient physics records;
receiving calibration information;
determining a delivered dose rate from the calibration information and the delivered radiotherapy treatment information including the dose, irradiation time and position information;
comparing the delivered dose rate and the delivered radiotherapy treatment information including the dose, irradiation time and position information to the dose, dose rate, irradiation time and position information of the radiotherapy treatment plan to generate a graphical representation of one or more of the delivered dose rate and the delivered radiotherapy treatment information including the dose, irradiation time and position information versus the dose, dose rate, irradiation time and position information of the planned radiotherapy treatment information; and
outputting the graphical representation of one or more of the delivered dose rate and the delivered radiotherapy treatment information including the dose, irradiation time and position information versus the dose, dose rate, irradiation time and position information of the planned radiotherapy treatment information.

9. The radiotherapy dose analysis method according to claim 8, wherein the radiotherapy treatment of the delivered radiotherapy treatment information and the planned radiotherapy treatment information comprises a flash radiotherapy treatment.

10. The radiotherapy dose analysis method according to claim 8, wherein:

the dose rate of the planned radiotherapy treatment information is determined from the dose, irradiation time and position information of planned radiotherapy treatment information.

11. The radiotherapy dose analysis method according to claim 10, wherein the delivered radiotherapy treatment information is determined from one or more treatment delivery records of a radiotherapy delivery system.

12. The radiotherapy dose analysis method according to claim 8, further comprising:
   extracting fractions of voxels in two or three dimensions that are above one or more of a delivered dose threshold and a dose rate threshold from statistical parameters including one or more of the delivered dose threshold and the dose rate threshold.

13. The radiotherapy dose analysis method according to claim 8, further comprising determining the planned radiotherapy treatment information including the dose, dose rate, irradiation time and position information from patient physics information.

14. Computing device executable instructions stored on one or more computing device readable media that when executed by one or more processors perform a radiotherapy dose analysis method comprising:
   determining delivered radiotherapy treatment information including dose, irradiation time and position information;
   determining planned radiotherapy treatment information including dose, dose rate, irradiation time and position information from a radiotherapy treatment plan and patient physics records;
   receiving calibration information;
   determining a delivered dose rate from the calibration information and the delivered radiotherapy treatment information including the dose, irradiation time and position information;
   comparing the delivered dose rate and the delivered radiotherapy treatment information including the dose, irradiation time and position information to the dose, dose rate, irradiation time and position information of the radiotherapy treatment plan to generate a graphical representation of one or more of the delivered dose rate and the delivered radiotherapy treatment information including the dose, irradiation time and position information versus the dose, dose rate, irradiation time and position information of the planned radiotherapy treatment information; and
   outputting the graphical representation of one or more of the delivered dose rate and the delivered radiotherapy treatment information including the dose, irradiation time and position information versus the dose, dose rate, irradiation time and position information of the planned radiotherapy treatment information.

15. The computing device executable instructions stored on the one or more computing device readable media that when executed by the one or more processors perform the radiotherapy dose analysis method according to claim 14, wherein:
   the dose rate of the planned radiotherapy treatment information is determined from the dose, irradiation time and position information of planned radiotherapy treatment information.

16. The computing device executable instructions stored on the one or more computing device readable media that when executed by the one or more processors perform the radiotherapy dose analysis method according to claim 15, wherein the delivered radiotherapy treatment information is determined from one or more treatment delivery records of a radiotherapy delivery system.

17. The computing device executable instructions stored on the one or more computing device readable media that when executed by the one or more processors perform the radiotherapy dose analysis method according to claim 14, further comprising:
   extracting fractions of voxels in two or three dimensions that are above one or more of a delivered dose threshold and a dose rate threshold from statistical parameters including one or more of the delivered dose threshold and the dose rate threshold.

* * * * *